United States Patent
Grunewald

(12) 
(10) Patent No.: US 6,688,159 B1
(45) Date of Patent: Feb. 10, 2004

(54) METHOD AND DEVICE FOR DETERMINING THE GAS CONCENTRATIONS IN A GAS MIXTURE

(76) Inventor: Axel-Ulrich Grunewald, Niedwiesenstrasse 27E, D-60431 Frankfurt am Main (DE)

( * ) Notice: Subject to any disclaimer, the term of this patent is extended or adjusted under 35 U.S.C. 154(b) by 46 days.

(21) Appl. No.: 10/110,577

(22) PCT Filed: Oct. 9, 2000

(86) PCT No.: PCT/DE00/03457
§ 371 (c)(1),
(2), (4) Date: Apr. 11, 2002

(87) PCT Pub. No.: WO01/27604
PCT Pub. Date: Apr. 19, 2001

(30) Foreign Application Priority Data

Oct. 13, 1999 (DE) ......................................... 199 49 327

(51) Int. Cl.⁷ ........................ G01N 25/18; G01N 27/18; G01N 31/00; G01R 23/00; G01K 13/00
(52) U.S. Cl. ...................... 73/25.03; 73/23.2; 73/25.01; 702/24; 702/30
(58) Field of Search ............................. 73/25.03, 23.2, 73/25.01; 702/24, 25, 30, 77

(56) References Cited

U.S. PATENT DOCUMENTS

| | | | | |
|---|---|---|---|---|
| 4,164,862 | A | | 8/1979 | Jackson ........................ 73/27 R |
| 4,399,684 | A | * | 8/1983 | Advani et al. ................ 73/1 G |
| 5,265,459 | A | * | 11/1993 | Cohen ......................... 73/25.03 |
| 5,379,630 | A | * | 1/1995 | Lacey ......................... 73/25.03 |
| 5,515,714 | A | | 5/1996 | Sultan et al. ................ 73/25.01 |
| 5,583,784 | A | * | 12/1996 | Kapust et al. ............... 364/484 |
| 5,602,751 | A | * | 2/1997 | Edelblute .................... 364/485 |
| 5,925,815 | A | * | 7/1999 | Jones et al. ................. 73/25.03 |
| 6,065,328 | A | * | 5/2000 | Dayton et al. .............. 73/25.01 |
| 6,094,968 | A | * | 8/2000 | Scheufler et al. ............. 73/23.2 |
| 6,159,255 | A | * | 12/2000 | Perkins ........................ 44/300 |
| 6,345,234 | B1 | * | 2/2002 | Dilger et al. .................. 702/24 |
| 6,442,996 | B1 | * | 9/2002 | Thurston et al. ........... 73/24.01 |

FOREIGN PATENT DOCUMENTS

| | | |
|---|---|---|
| DE | 37 11 511 | 6/1988 |
| DE | 198 08 681 | 9/1991 |
| DE | 195 35 819 | 3/1997 |

\* cited by examiner

*Primary Examiner*—Hezron Williams
*Assistant Examiner*—David J. Wiggins
(74) *Attorney, Agent, or Firm*—Collard & Roe, P.C.

(57) ABSTRACT

The invention is directed to a method of determining gas concentrations in a gas mixture comprising more than one component, in which thermal conductivities of the gas mixture are determined at different temperatures, deriving therefrom the individual gas concentrations.

Figure 1:
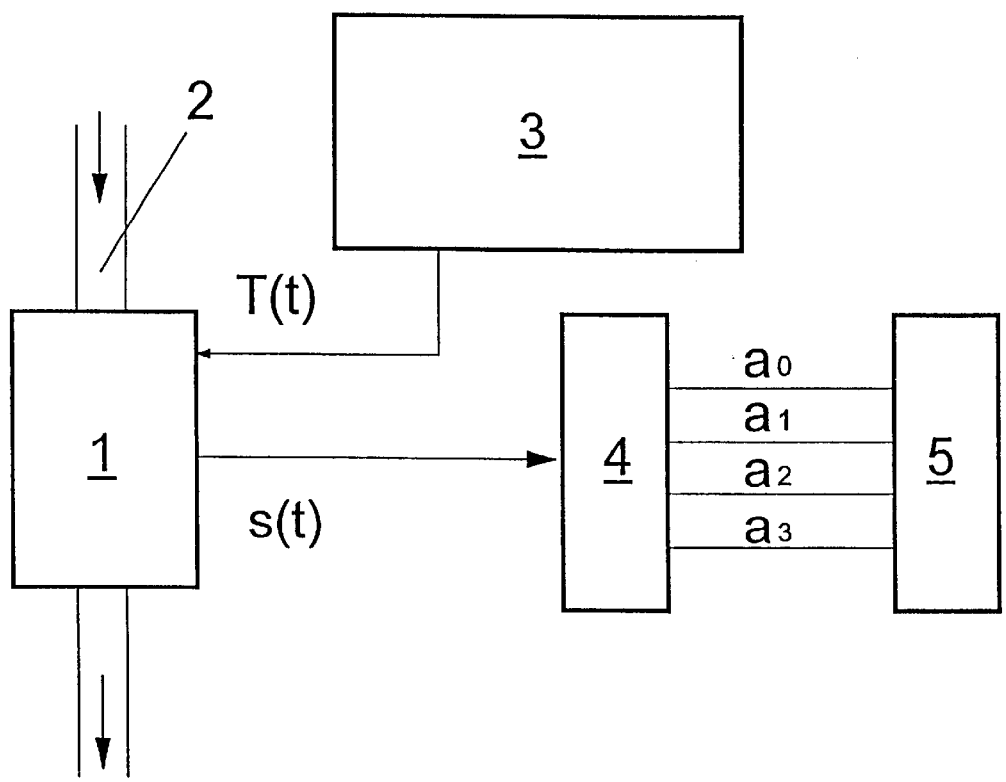

The invention aims to improve upon this method by enabling the accuracy of measurement to be enhanced, the sensitivity to external influences to be diminished, and the constructional expenditure of a measuring apparatus to be reduced. According to the invention, this is accomplished by determining the thermal conductivities at a temperature level varying periodically as a function of time between a minimal and a maximal temperature value and determining continuously, as a function of time, the thermal conductivities obtained with the variation of temperature with time, and by subjecting the time function of the thermal conductivity to a Fourier analysis and determining from the coefficients of said Fourier analysis the concentrations of the gas components. The device for subjecting the sensor element to predetermined temperature values is a temperature generator adapted to act upon the sensor element continuously with a periodic variation of temperature with time. Arranged downstream of the sensor element is a Fourier analyzer adapted to receive a sensor signal indicative of the thermal conductivity of the gas mixture passed through the sensor. An evaluation unit connected downstream of the Fourier analyzer determines the gas concentrations from the coefficients of the Fourier analysis.

7 Claims, 2 Drawing Sheets

METHOD AND DEVICE FOR DETERMINING THE GAS CONCENTRATIONS IN A GAS MIXTURE

CROSS REFERENCE TO RELATED APPLICATIONS

Applicant claims priority under 35 U.S.C. §119 of German Application No. 199 49 327.8 filed Oct. 13, 1999. Applicant also claims priority under 35 U.S.C. §120 of PCT/DE00/03457 filed Oct. 9, 2000. The international application under PCT article 21(2) was not published in English.

This invention relates to a method of and an apparatus for determining the gas concentrations in a gas mixture according to the prior art portions of the method and substance claims, respectively.

Thermal conductivity defines generally the heat flow relationship occurring as a result of a temperature difference between a heat source and a heat sink. Thermal conductivity is related specifically to the area through which the heat is passed and the distance between heat source and heat sink. Where gases are involved, the coefficient of thermal conductivity depends in a complex manner on the temperature (temperature level), the molecular weight of the gas and the degree of freedom of the gas molecules. In the kinetic interpretation of the coefficient of thermal conductivity of gases, also the radius (mean radius) of the molecules is involved. As a general rule, the thermal conductivity of gases increases with rising temperature and decreases with increasing molecular mass.

The dependence of thermal conductivity upon the molecular parameters briefly outlined in the foregoing is utilized for the determination of gas concentrations in a gas mixture. From DE 37 11 511 C1 there is known a method of determining the gas concentrations in a gas mixture and a sensor for measuring the thermal conductivity of a gas mixture. Very generally, this method makes use of the difference in the thermal conductivity of different gases. The analyzer finding application in this method is comprised of a heat source and a heat sink through which a gas mixture is adapted to be passed. By passing current through a resistance heating element serving as heat source, it is heated to a temperature exceeding the temperature of its environment. Via a heat conducting path determined by the geometry of the arrangement, the gas mixture conducts heat from the heat source to a heat sink maintained at a constant temperature level. As a result of the heat transport from the heat source to the heat sink energy is withdrawn from the heat source, this energy being a measure of the thermal conductivity of the gas mixture and suited for measurement by appropriate methods.

As mentioned in the foregoing, the thermal conductivity of a gas is dependent on temperature. In order to cancel the effects of the temperature coefficient of the heat conduction, the detector cell is placed under thermostatic control, i.e., maintained at a constant temperature by electronic regulation. In addition to being determined by the temperature of the detector cell, the mean gas temperature in the heat conducting path is also determined by the temperature of the heat source. Therefore this temperature is likewise maintained constant or adjusted for repeatability.

If the gas mixture comprises only two components, it will suffice to measure the thermal conductivity at a single temperature level. The mean temperature value between heat source and heat sink shall be assumed as temperature level. By definition it is also possible to specify as temperature level the value of the heat source or of the heat sink.

If the gas mixture comprises more than two components, meaning that the concentrations (ratio of the partial pressures) of more than two different gases have to be determined, it is necessary according to the method known from the specification referred to above to determine the thermal conductivities at plural stationary temperatures (temperature levels). Generally speaking, this means that to determine the gas concentrations in a mixture consisting of N (>2) components, it is necessary to determine the thermal conductivity of the gas mixture at least at N−1 gas temperatures in order to then compute from the measured thermal conductivity values the individual gas concentrations using known mathematical methods for solving nonlinear systems of equation. In a modification of this known method it is proposed measuring the thermal conductivity of the gas mixture at least at N gas temperatures in order to identify the unknown gas components.

The sensor usable in this known method for measuring the thermal conductivity of the gas mixture stream is comprised of a substrate made of silicon and having a thickness of some 100 micrometers. Applied to this substrate is an insulating layer which in turn has applied to it by vapor deposition or sputtering meander-shaped thin-film resistors. In the area underneath the thin-film resistors the insulating layer is etched, producing a cavity in the substrate which forms the lower part of the sensor's measuring chamber. Resting on the substrate carrying the thin-film resistors is a silicon coating into which another cavity is etched in the region of the thin-film resistors, said cavity forming the upper part of the measuring chamber. The silicon layer has an opening which, serving as a diffusion duct, enables the gas mixture to enter the measuring chamber.

To implement the known method with the sensor, it is necessary that, for the determination of multiple-component gas mixtures, thermal conductivity measurements be performed at correspondingly multiple stationary temperature levels. This involves heating the sensor element each time to a predetermined temperature value for subsequent measurement of the corresponding thermal conductivity. To reduce the heating times to a minimum, a low sensor mass is required so that the resultant thermal time constant is as low as possible. Alternatively, it is also possible for the thermal conductivity measurements to be performed by means of a corresponding number of sensors which are heated to the different temperature levels in parallel. However, this second variant of the prior known method necessitates an increased number of components. The process of successively heating one sensor element to different temperature levels requires precise accuracy to minimize external influences which, to be adequately shielded, incurs increased expenditure.

Accordingly, it is an object of the present invention to improve upon a method of and an apparatus for determining gas concentrations in a gas mixture according to the prior art portions of the method and substance claims, respectively, in such manner as to enable the accuracy of measurement to be enhanced, the sensitivity to external influences to be diminished, and the constructional expenditure of the measuring apparatus to be reduced.

This object is accomplished by the characterizing features of the method and substance claims, respectively. Further features of the invention will become apparent from the respective subclaims.

According to the present invention provision is made for the thermal conductivity of the gas mixture to be determined continuously at a temperature level varying periodically between a minimal and a maximal temperature value. This means that a temperature generator heats the sensor used in the determination of the thermal conductivity periodically, alternating between the minimal and maximal value of the temperature level. In the process, the temperature difference between heat source and heat sink of the sensor may remain constant—the essential point being that the mean temperature value between source and sink alternates periodically between the minimal and maximal value, hence oscillating at a predetermined amplitude about a mean value.

According to a preferred embodiment of the invention, the thermal conductivity of the gas mixture is determined with a temperature variation with time configured as a harmonic function (sine function) between minimal and maximal temperature values. To implement the method, a sensor of a type known in the art may be employed, in particular a sensor of the type described in DE 37 11 511 C1.

An output signal of the sensor is a measure of the thermal conductivity of the sensor element heated periodically and in particular with a harmonic temperature-time function. By reason of the complex relationships between thermal conductivity and molecular mass, molecular size and mean temperature (temperature level), the sensor signal indicative of the thermal conductivity of the gas mixture will be periodic for a gas mixture with N>2 components, yet will exhibit a distorted characteristic relative to the temperature profile. It is thus possible to determine the concentrations of the gas components (the ratio of the partial pressures to one another) from the variation of the sensor signal with time, i.e., the thermal conductivity values at a given variation of temperature with time.

According to a preferred embodiment of the present invention, determination of the thermal conductivity involves exposing the sensor to a harmonic (sinusoidal) variation of temperature with time and subjecting the sensor signal indicative of the thermal conductivity of the gas mixture to a harmonic analysis (expansion into a series of trigonometric functions=Fourier series). Considering that the thermal conductivity is determined at a harmonic (sinusoidal) variation of temperature, the sensor signal representative of the thermal conductivity of the gas mixture is composed of a sum of harmonic functions of time whose frequencies/periods are an integral multiple of the fundamental frequency/period of the temperature-time function applied to the sensor element. The individual coefficients (amplitudes) with which the harmonic content (the spectrum) has to be weighted in order to yield in the sum the sensor signal are therefore a measure of the concentrations (ratio of the partial pressures) of the individual components of the gas mixture.

An embodiment of the present invention will be described in more detail in the following with reference to the accompanying drawings. In the drawings, FIG. 1 is a schematic diagram to illustrate the implementation of the method of the invention; and FIG. 2 shows graphical representations of the temperature applied to the sensor element, of the sensor signal indicative of the thermal conductivity of the gas mixture, each plotted as a function of time, and of the individual Fourier coefficients of the sensor signal indicative of the thermal conductivity.

A sensor element 1 constructed in a manner known in the art for determining the thermal conductivity s of a gas stream 2 directed through the sensor element 1 is operatively associated with a temperature generator 3 (FIG. 1). The temperature generator 3 is operable to apply to the sensor element 1 a predetermined periodic temperature pro-file, particularly a temperature profile corresponding to a harmonic function of time. Hence the sensor element 1 determines the thermal conductivity of the gas stream 2 at different temperatures/temperature levels T(t).

Figure 2:
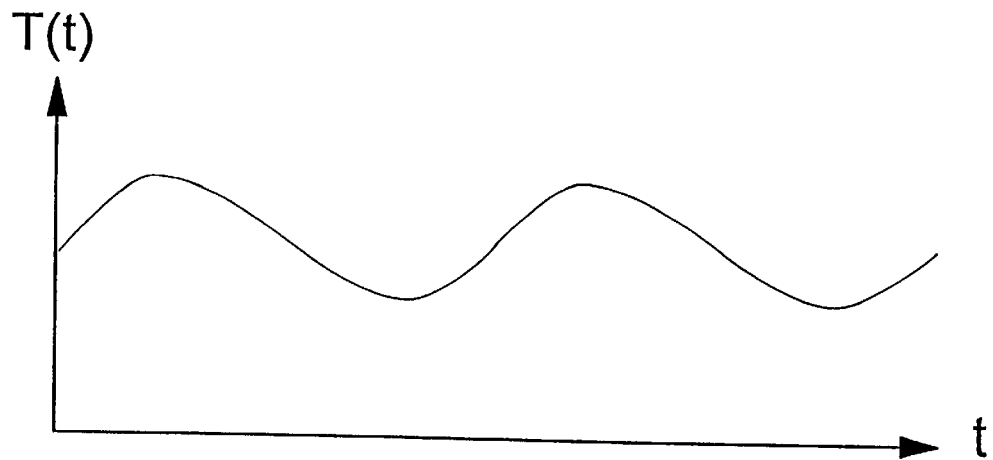
Figure 2:
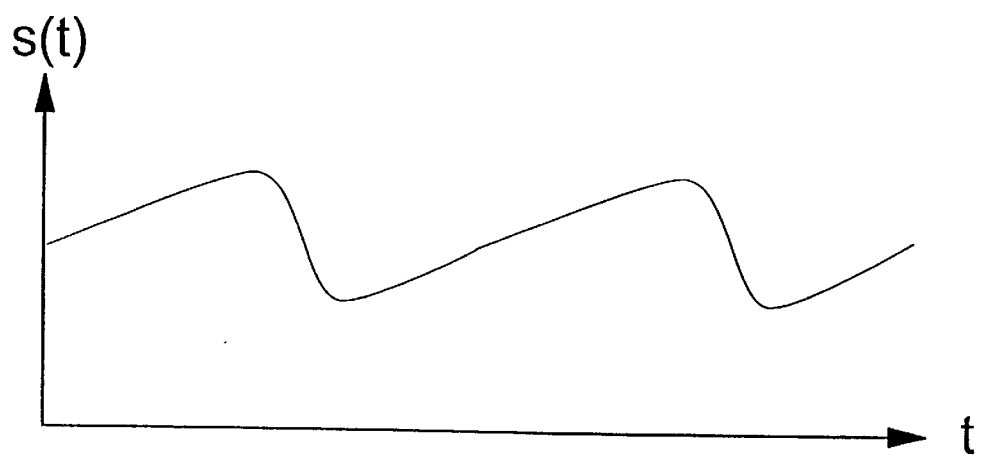
Figure 2:
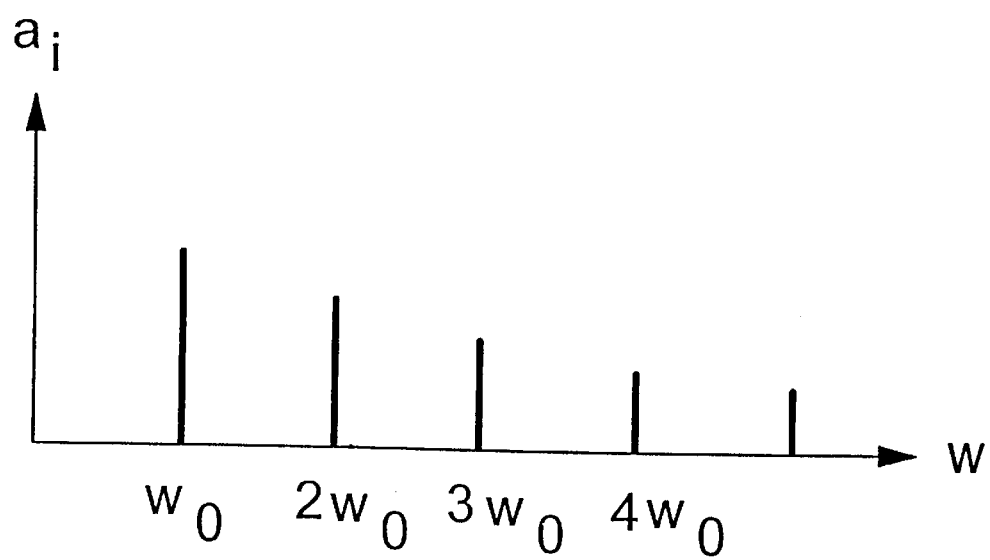

FIG. 2 shows a harmonic temperature variation with time T(t) to which the sensor element 1 is exposed. The period of the temperature variation with time of this harmonic function T(t) is $T = 2\pi/w_0$.

The signal s(t) indicative of the thermal conductivity of the gas stream 2 passed through the sensor element 1 is directed to a Fourier analyzer 4 capable of determining the Fourier coefficients $a_0$, $a_1$, $a_2$, $a_3$, ... The sensor element 1 being exposed to a harmonic temperature-time profile T(t), the signal s(t) indicative of the thermal conductivity of the gas stream 2 passed through the sensor element 1 is expressable as:

$$s(t) = a_0/2 + \sum_{i=1}^{\infty} a_i \cdot \sin(i \cdot w_0 \cdot t + \alpha_i)$$

It will be seen that with the above approach the signal s(t) indicative of the thermal conductivity of the gas stream 2 is represented as a sum of harmonics of the integral multiple frequencies $i \cdot W_0$, weighted by different amplitude factors $a_i$. The quantity $\alpha_i$ used in the above summation represents a phase factor.

If $$a_i = \sqrt{(A^2_i + B^2_i)} \text{ and } \tan \alpha_i = A_i/B_i$$

then $$A_i = 2/T \cdot \int_{-T/2}^{+T/2} s(t) \cdot \cos(i \cdot w_0 \cdot t) dt$$

and $$B_i = 2/T \cdot \int_{-T/2}^{+T/2} s(t) \cdot \sin(i \cdot w_0 \cdot t) dt$$

where i=0, 1, 2, 3, . . .

The signal characteristic s(t) resulting with a temperature-time profile T(t) is shown schematically in FIG. 2. FIG. 2 further shows in a third graph the coefficients $a_i$ allocatable to the individual frequencies $i \cdot w_0$ and determinable by the summation represented above.

With the Fourier transformation of the sensor signal s(t) indicative of the thermal conductivity of the gas mixture as disclosed in the invention, individual factors (Fourier coefficients) are obtained which serve to determine the concentration of the components of the gas mixture. To identify individual types of gas and their concentration percentages, provision may be made for an evaluation unit 5 connected downstream of the Fourier analyzer 4, which stores values for comparison with the Fourier coefficients $a_i$ obtained by the Fourier transformation of a given signal s(t).

In the method of the invention, the Fourier coefficients $a_i$ are expanded until a predetermined order n. The order is selected so that the coefficients with i>n are negligible, i.e., they do not noticeably contribute to the representation of s(t).

List of References

1 Sensor Element
2 Gas stream (Gas Mixture)

3 Temperature Generator
4 Fourier Analyzer
5 Evaluation Unit
t(t) Variation of Temperature with Time (Temperature Generator 3)
s(t), s Signal of Sensor Element 1 (Thermal Conductivity)
$a_i$ Fourier Coefficient

What is claimed is:

1. A method of determining the gas concentrations in a gas mixture comprising more than one component, in which thermal conductivities of the gas mixture are determined at different temperatures, deriving therefrom the individual gas concentrations, characterized by the steps of determining the thermal conductivities at a temperature level varying periodically as a function of time (T(t)) between a minimal and a maximal temperature value and determining continuously, as a function of time (t), the thermal conductivities (s(t)) obtained with the variation of temperature with time (T(t)), and subjecting the time function of the thermal conductivity (s(t)) to a Fourier analysis and determining from the coefficients ($a_i$) of said Fourier analysis the concentrations of the gas components.

2. The method as claimed in claim 1, characterized by the step of determining the thermal conductivity (s(t)) with a harmonic variation of temperature with time (T(t)).

3. The method as claimed in claim 1, characterized by the step of subjecting a signal indicative of the thermal conductivity (s(t)) of the gas mixture to said Fourier analysis.

4. The method as claimed in claim 1, characterized by the step of comparing the coefficients ($a_i$), obtained by the Fourier analysis, of the gas mixture to be determined with values obtained by a calibration process.

5. An apparatus for implementing the method of claim 1, with a sensor element for determining the thermal conductivity of a gas mixture adapted to be passed through the sensor and a device for subjecting the sensor element to predetermined temperature values, characterized in that said device for subjecting the sensor element (1) to predetermined temperature values is a temperature generator (3) adapted to act upon the sensor element (1) continuously with a periodic variation of temperature with time (T(t)), and that downstream of the sensor element (1) there is connected a Fourier analyzer (4) adapted to receive a sensor signal (s(t)) indicative of the thermal conductivity of the gas mixture (2) passed through said sensor.

6. The apparatus as claimed in claim 5, characterized in that the temperature generator (3) is operable to apply to the sensor element (1) a harmonic variation of temperature with time (T(t)).

7. The apparatus as claimed in claim 5, characterized in that downstream of the Fourier analyzer (4) is an evaluation unit (5) which enables the concentrations of the gas mixture to be determined by making a comparison between the coefficients (ai) of the signal (s(t)) of the thermal conductivity obtainable by Fourier analysis and values obtained by a calibration process.

* * * * *